(12) United States Patent
Epshtein et al.

(10) Patent No.: US 7,582,294 B2
(45) Date of Patent: Sep. 1, 2009

(54) MEDICAMENT FOR TREATING PROSTATE DISEASES

(75) Inventors: Oleg Iliich Epshtein, Moscow (RU); Evgeny Danilovich Goldberg, Tomsk (RU); Alexandr Mikhailovich Dygay, Tomsk (RU)

(73) Assignee: Oleg Oliich Epshtein, Moscow (RU)

( * ) Notice: Subject to any disclaimer, the term of this patent is extended or adjusted under 35 U.S.C. 154(b) by 91 days.

(21) Appl. No.: 10/522,653

(22) PCT Filed: Aug. 2, 2002

(86) PCT No.: PCT/RU02/00365

§ 371 (c)(1), (2), (4) Date: Jan. 22, 2005

(87) PCT Pub. No.: WO2004/012764

PCT Pub. Date: Feb. 12, 2004

(65) Prior Publication Data

US 2005/0266007 A1 Dec. 1, 2005

(51) Int. Cl.
*A61K 39/395* (2006.01)
*C07K 16/00* (2006.01)

(52) U.S. Cl. .............. 424/130.1; 424/141.1; 530/387.1; 530/388.1

(58) Field of Classification Search .............. None
See application file for complete search history.

(56) References Cited

U.S. PATENT DOCUMENTS

| 5,629,286 A | 5/1997 | Brewitt |
| 5,741,488 A * | 4/1998 | Feldman et al. .......... 424/154.1 |
| 2002/0001588 A1 * | 1/2002 | Sinha ...................... 424/178.1 |
| 2008/0025985 A1 | 1/2008 | Iliich et al. |

FOREIGN PATENT DOCUMENTS

| EP | 0652014 A1 | 5/1995 |
| RU | 2137483 C1 | 9/1999 |
| RU | 2144370 C1 | 1/2000 |
| SU | 1331508 A1 | 8/1987 |
| SU | 1730144 A1 | 4/1992 |

OTHER PUBLICATIONS

Davenas et al., Nature, 1988, 333:816-818.*
Epshtein et al., Bulletin of experimental Biology and Medicine, 1999, 5:493-495.*
International Search Report from International Application No. PCT/RU02/00365, filed Aug. 2, 2002, mailed on Dec. 5, 2002.
Kuznik, R. I. et al., "Cytomedines and their Role in Regulation of Physiological Functions," Uspekhi Sovremennoi Biologii, 1995, vol. 115, No. 3, pp. 353-367.
Frimel, G., ed., "Immunological Methods," Moscow, Medicina Publishing House, 1987, pp. 9-33.
Register of Pharmaceuticals in Russia, Encyclopedia of Pharmaceuticals (in Russian), Moscow, 2000, pp. 358-359.
Sensabaugh, G. F. et al., "Seminal Plasma Protein p30: Simplified Purification and Evidence for Identity with Prostate Specific Antigen," J. Urol., vol. 144, pp. 1523-1526, 1990.
Schwabe, W., "German Homoeopathic Pharmacopoeia (Homoeopathisches Arzneibuch)," Stuttgart, Translation of the 5th Supplement (1991) to the 1978 edition.

* cited by examiner

*Primary Examiner*—Ilia Ouspenski
(74) *Attorney, Agent, or Firm*—Kaplan Gilman & Pergament LLP

(57) ABSTRACT

A medicament based on antibodies contains an activated form of ultra-low doses of monoclonal, polyclonal, or natural antibodies to the prostate-specific antigen, the activated form being prepared by multiple consecutive dilutions and exposure to external factors, preferably according to homeopathic technology. In order to obtain the antibodies, the prostate-specific antigen isolated from the prostatic tissues of cattle or prepared synthetically is employed; a mixture of various, mostly centesimal, homeopathic dilutions is used. The method of treating diseases of the urogenital sphere consists in using activated forms of ultra-low doses of antibodies to prostate-specific antigen prepared by multiple consecutive dilutions and exposure to external factors.

6 Claims, No Drawings

MEDICAMENT FOR TREATING PROSTATE DISEASES

FIELD OF THE INVENTION

The preset invention relates to the field of medicine and can be used for the treatment and prevention of diseases of the urogenital system, mainly of the prostate.

BACKGROUND OF THE INVENTION

It is a well-known practice of the treatment of pathologic syndromes by the use of antibodies (SU 1331508 A, A 61 K 39/00, 1984; SU 1730144 A1, C 12 N 7/00, 1992).

Pharmaceuticals (sera, immunoglobulins) based on antibodies and used in therapeutic doses (see, for instance, Register of Pharmaceuticals in Russia, Encyclopedia of Pharmaceuticals (in Russian), 2000, Moscow, pp. 358-359) are also well known.

However, the use of such preparations may be accompanied by undesired side effects caused by the injection of substantial doses of foreign proteins into the body.

A method of treating prostate diseases by administering a preparation obtained from the prostates of cattle (see Cytomedines and their Role in Regulation of Physiologic Functions, Uspekhi Sovremennoi Biologii, 1995, vol.115, No. 3, p.353) is well known.

DESCRIPTION OF THE INVENTION

The present invention is directed at the development of an efficient method of treating the diseases of the urogenital system, mostly of the prostate, and of a relevant medicament, by the use of activated forms of antibodies.

The formulated objective is attained by the use of a medicament containing an activated form of ultra-low doses of monoclonal, polyclonal or natural antibodies to prostate-specific antigen, the medicament being prepared by multiple consecutive dilutions and by exposure to external factors, mostly following homeopathic technology.

For preparing the antibodies we used prostate-specific antigen isolated from the tissues of animal prostates or prepared by a synthetic method.

Preferably, a mixture of various, mostly centesimal, homeopathic dilutions should be employed.

The method of treating the diseases of the urogenital system by administering a medicament obtained on the basis of polypeptides isolated from the prostatic tissue consists in the use of activated forms of ultra-low doses of antibodies to prostate-specific antigen, the activated forms being prepared by multiple consecutive dilutions and exposure to external factors.

The agent prepared in accordance with the present invention is a new pharmaceutical, which is characterized by a prominent specific pharmacologic activity, the absence of side effects with the therapeutic action retained, environmental purity, and low production cost, which makes it possible to treat efficiently diseases of the urogenital system, mostly of the prostate.

EMBODIMENTS OF THE INVENTION

The new medicament is preferably prepared as follows.

The prostate-specific antigen is isolated from the homogenate of the prostatic tissue of cattle by the method of gel filtration (see, for example, Sensabaugh, G F, Blake, E T, "Seminal Plasma Protein p30: Simplified Purification and Evidence for Identity with Prostate Specific Antigen", J. Urol. 144:1523-1526, 1990).

The resultant polypeptide is used as an immunogen for immunization of laboratory animals to produce immune antibodies, or in hybridoma technology designed to produce monoclonal antibodies. These antibodies are purified by affinity chromatography.

The method of preparation of immune and polyclonal antibodies is described, for instance, in the book edited by G. Frimel, Immunological Methods (in Russian), Moscow, Meditsina, 1987, pp. 9-33. The isolated antibodies to prostate specific antigen are subjected to multiple consecutive dilutions and exposure to mechanical factors to produce ultra-low or low doses, for instance, by homeopathic technology (see W. Schwabe, "Homöopathisches Arzneibuch", Stuttgart, 1978). This technique enables a uniform decrease in concentration through consecutive dilution of 1 volumetric part of the initial matter (antibodies) in 9 volumetric parts (for decimal dilution, D) or in 99 volumetric parts (for centesimal dilution, C) of a neutral solvent together with multiple vertical shaking of each solution; the advantages of various containers for each subsequent dilution are used. Finally, this technique gives the required dose (potency).

The external treatment in the course of concentration reduction can also be executed by exposure to ultrasonic, electromagnetic, or other physical factors.

The resultant medicines are used mostly in the dosage forms and dilutions adopted in the homeopathic practice: as alcoholic and aqueous solutions or as tablets (granules) prepared by impregnating the carrier contained in the dosage form by the potentised solution to saturation; also, the potentised solution can be added directly to a liquid dosage form.

EXAMPLE 1

In studies of the action of activated forms of ultra-low doses of antibodies (AB) to prostate-specific antigen (PSA) on the state of the rat prostate in acute aseptic inflammation, a morphometric analysis of the prostate sections was run; the density of the prostate and the levels of zinc on the $7^{th}$ day after the operation of prostate stitching with a silk thread were assessed. The animals of the test group received polyclonal immune antibodies to the bovine PSA in a mixture of homeopathic dilutions C12+C30+C200 intragastrically: per 1.5 ml over a period of 3 days before and 7 days after the operation.

TABLE 1

Effect of AB to PSA on the state of the Rat Prostate in Aseptic Inflammation

| Index assessed | Control | Experiment |
| --- | --- | --- |
| Morphometry: proportion of structural elements of the prostate on acute inflammation, %: | | |
| vessels | 2.98 ± 0.61 | 1.84 ± 0.25* |
| edema | 17.3 ± 0.63 | 12.32 ± 1.29* |
| Density of the prostate, g/cm$^3$ | 1.10 ± 0.03 | 1.92 ± 0.02* |
| Concentration of zinc ions, mg/100 g | 0.49 ± 0.11 | 2.01 ± 0.37* |

Note.
*The data are significantly different from those of the Control; $p < 0.05$.

The experimental results listed here indicate that antibodies to PSA attenuate the manifestations of acute inflammatory reaction in the prostate and improve the functional state of the gland in aseptic inflammation.

EXAMPLE 2

Prostatotropic effect of activated forms of ultra-low doses of antibodies to PSA was studied in the model of gonadectomized infantile male rats (under the conditions of androgenic insufficiency) receiving testosterone propionate.

Monoclonal immune antibodies to human PSA were administered intragastrically (0.5 ml/100 g body weight) in a mixture of C12+C30+C200 homeopathic dilutions against the background of testosterone propionate injections to gonadectomized infantile male rats within a period of 7 days beginning with the day following gonadectomy.

TABLE 2

Effect of Antibodies to PSA on the Androgenic Action of Testosterone Propionate in Gonadectomized Male Rats

| Test group | Weight coefficients of organs, mg/g | | Weight coefficients of organs, % of control | |
|---|---|---|---|---|
| | Ventral Prostate | Seminal vesicles | Ventral prostate | Seminal vesicles |
| Control 1 (intact animals) | 0.21 ± 0.02 | 0.12 ± 0.01 | 100 | 100 |
| Control 2 (castrated animals) | 0.09 ± 0.03* | 0.08 ± 0.01* | 42.8 | 66.6 |
| Control 3 + testosterone propionate + solvent | 0.17 ± 0.02* | 0.28 ± 0.01* | 188.8 | 362.5 |
| Testosterone propionate + anti-PSA | 0.23 ± 0.01 | 0.29 ± 0.02 | 135.2 (as against Control 3) | 103 (as against Control 3) |

Note.
*The differences are significant as compared with the Control; $p < 0.05$.

The experimental results given in Table 2 show that the antibodies to PSA feature pronounced prostatotropic activity and stimulate the androgenic effect of an androgen on the prostate.

EXAMPLE 3

Patient P., aged 31, applied to the urologist with a complaint about disagreeable feelings and dragging pain along the urethra, at the bottom of the abdomen, trusting pain in the perineum, frequent micturate urges, and periodic dysuria. The patient had been noting these phenomena for 3 years; the disease exacerbated 3-5 times a year, particularly after becoming cold and after alcohol abuse. A detailed interview also revealed the lessening of satisfaction from coitus, impaired erection, and pain in the perineum after coitus. Rectal examinations detected sore soft prostate. Bacteriological studies of the prostatic secretion and immunofluorescent analysis for *Chlamidia trachomatis* found no pathogenic microorganisms. Diagnosis: chronic prostatitis. Prescription: a mixture of polyclonal antibodies to the human prostate-specific antigen in a C1000 homeopathic dilution, 1 tablet daily for 1 month. Ten days after the beginning of the treatment the patient marked a noticeable weakening of pain and improved urination. Three weeks after the beginning of the treatment the patient indicated the disappearance of problems in the sexual sphere. After the end of the treatment a complete clinical remission of the disease was established. Recommendation: intake of the preparation 2 times weekly over a period of 3 months. Catamnesis: one exacerbation within a year, the inflammation being stopped in a short time by daily intake of the preparation for 5 days.

EXAMPLE 4

Patient A. (male), aged 60, appealed to the urologist with a complaint about the sensation of incomplete emptying of the urinary bladder, frequent and interrupted urination, need to strain during urination, bradyuria, nycturia (4-5 times). The symptoms had been lasting for 5 years with aggravation. There had been no episodes of acute retention of urine. The filling out the International scale of symptoms of prostate diseases (I-PSS) gave a total score of 25. Rectal palpation revealed a painless enlarged prostate; the gland had a soft elastic consistence. According to the ultrasonic examination, the volume of the residual urine was 100 ml. Diagnosis: benign hyperplasia (adenoma) of the prostate. The patient refused from operative treatment. Prescription: a mixture of polyclonal antibodies to the human prostate-specific antigen in C30+C200+C1000 homeopathic dilutions, 1 tablet daily for 1 month. The second examination one month later showed that the intensity of the dysuric symptoms decreased markedly; the total score of I-PSS scale reduced to 15 points. The ultrasonic examination indicated that the volume of the residual urine was 30 ml. Recommendation: further intake of the preparation two times a week.

The invention claimed is:

1. A medicament for treating Benign Prostatic Hyperplasia or prostatitis, said medicament comprising a homeopathically activated form of at least one monoclonal, polyclonal, or natural antibody to prostate specific antigen (PSA).

2. The medicament according to claim 1, wherein said homeopathically activated form of monoclonal, polyclonal or natural antibody comprises a homeopathic dilution prepared from an initial solution containing at least one monoclonal, polyclonal or natural antibody to prostate-specific antigen (PSA).

3. The medicament of claim 2, wherein said initial solution contains at least one monoclonal, polyclonal or natural antibody to prostate-specific antigen (PSA) isolated from prostatic tissues of cattle or prepared synthetically.

4. The medicament according to claim 3, wherein said homeopathic dilution comprises one or more centesimal homeopathic dilutions.

5. The medicament of claim 1, which is a medicament for treating Benign Prostatic Hyperplasia.

6. The medicament of claim 1, which is a medicament for treating prostatitis.

* * * * *

UNITED STATES PATENT AND TRADEMARK OFFICE
CERTIFICATE OF CORRECTION

PATENT NO. : 7,582,294 B2  Page 1 of 1
APPLICATION NO. : 10/522653
DATED : September 1, 2009
INVENTOR(S) : Epshtein et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 341 days.

Signed and Sealed this

Fourteenth Day of September, 2010

David J. Kappos
*Director of the United States Patent and Trademark Office*